(12) United States Patent
Arakawa

(10) Patent No.: US 6,893,157 B2
(45) Date of Patent: May 17, 2005

(54) RADIATION IMAGE OBTAINING SYSTEM AND RADIATION IMAGE DETECTOR

(75) Inventor: Satoshi Arakawa, Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 27 days.

(21) Appl. No.: 10/685,449

(22) Filed: Oct. 16, 2003

(65) Prior Publication Data

US 2005/0069091 A1 Mar. 31, 2005

(30) Foreign Application Priority Data

Oct. 16, 2002 (JP) ........................................ 2002/301582

(51) Int. Cl.[7] ................................................ A61B 6/08
(52) U.S. Cl. ........................ 378/205; 378/207; 378/62
(58) Field of Search .......................... 378/62, 154, 155, 378/162, 163, 164, 205, 207; 250/370.08, 370.09

(56) References Cited

U.S. PATENT DOCUMENTS 4,258,264 A  3/1981 Kotera et al. ............... 250/585
6,748,047 B2 *  6/2004 Gonzalez Trotter et al. ... 378/62
2002/0057762 A1  5/2002 Tanaka et al. ............... 378/205

FOREIGN PATENT DOCUMENTS

JP  56-11395 A  2/1981

* cited by examiner

Primary Examiner—David V. Bruce
Assistant Examiner—Courtney Thomas
(74) Attorney, Agent, or Firm—Sughrue Mion, PLLC

(57) ABSTRACT

A radiation image obtaining system that detects a radiation image of a subject by irradiation of radiation which has passed through the subject and a grid, in which a position of a radiation source with respect to a recording surface of a radiation image detector, and an angle of a central axis of radiation with respect to the recording surface, are obtained with a simple structure. Two lines, which pass through center positions of pinhole images, recorded in the radiation-image detector by irradiation thereof by the radiation which has passed through pinholes, and predetermined center positions of the pinholes, are obtained. The position of the radiation source with respect to the recording surface and the angle of the central axis of the radiation with respect to the recording surface are calculated, based on distances between the intersection of the two lines the center positions of the pinhole images.

15 Claims, 3 Drawing Sheets

RADIATION IMAGE OBTAINING SYSTEM AND RADIATION IMAGE DETECTOR

BACKGROUND OF THE INVENTION

1. Field of the Invention

The present invention relates to a radiation image obtaining system and a radiation image detector for detecting a radiation image by irradiation of radiation, emitted from a radiation source and which passes through a subject of imaging. Particularly, the present invention relates to a radiation image obtaining system and a radiation image detector for detecting a radiation image of a subject by irradiation of radiation which passes through a grid.

2. Description of the Related Art

In the field of medicine, radiation image obtaining systems are in wide use. The image obtaining systems comprise a radiation source and a radiation image detector. The radiation image detectors comprise a radiation image recording medium such as a stimulable phosphor sheet, a solid state radiation detector or the like, and detect radiation images recorded thereon as electric signals (refer to U.S. Pat. No. 4,258,264 and Japanese Unexamined Patent Publication No. 56 (1981)-11395).

Presently, use of the radiation image obtaining systems is not limited to that within imaging rooms of hospitals. For example, the systems are brought into an ICU unit of a hospital to obtain a great number of images within a short period of time. Alternatively, the systems are brought to patients and care recipients outside the hospital, to obtain radiation images at these locations.

Regarding the use of the radiation image obtaining systems described above, there are cases in which imaging is performed with a grid placed between a subject of imaging and the stimulable phosphor sheet, parallel to a recording surface of the radiation image detector. The grid is provided to prevent radiation, which has been dispersed by the subject, from irradiating the stimulable phosphor sheet. The grid is formed by alternately placing lead, which does not transmit radiation, and aluminum or wood, which transmits radiation, at a fine predetermined pitch. When imaging is performed using the grid, the radiation, which has been dispersed by the subject, is less likely to be irradiated onto the stimulable phosphor sheet. Therefore, contrast in the radiation image of the subject can be improved.

Regarding the use of radiation image obtaining systems employing the grids as described above, problems occur in the case that they are brought into the ICU unit to obtain a great number of images in a short period of time, or in the case that they are brought outside the hospital. These problems occur due to the fact that an angle of a central axis of the radiation, emitted from the radiation source, with respect to the radiation image detector cannot be maintained perpendicular. Therefore, the angle may change for every image. Also, the position of the radiation source with respect to the radiation image detector may not be appropriate. The above factors cause the radiation to be incident on the grid from an inappropriate direction, causing problems of false image detection and deterioration of image reproducibility. U.S. Patent Laid-Open No. 20020057762 discloses methods for solving the above problems. The methods disclosed in U.S. Patent Laid-Open No. 20020057762 involve: measuring the angle by using a device such as an electronic level for measuring horizontality or a projection type angle sensor; then adjusting the angle to be substantially perpendicular. However, the manufacturing costs of the system is increased due to the necessity to provide these measuring devices, and the structure of the system becomes complicated.

SUMMARY OF THE INVENTION

The present invention has been developed in view of the problems described above. It is an object of the present invention to provide a radiation image obtaining system and a radiation image detector that enables an angle of a central axis of radiation with respect to a recording surface of the radiation image detector to be perpendicular, and a position of a radiation source with respect to the radiation image detector to be appropriate, with a simple construction.

The radiation image obtaining system of the present invention comprises:

a radiation source;

a radiation image detector for recording a radiation image of a subject by irradiation thereof by radiation emitted from a radiation source, which has passed through the subject; and a grid provided between the radiation image detector and the radiation source, parallel to a recording surface of the radiation image detector;

an angle/position detection member provided between the radiation source and the radiation image detector, having at least two detection portions having a transmittance rate with respect to radiation emitted from the radiation source different from their surroundings, which are provided at predetermined positions with respect to the recording surface; and an angle/position calculating means for calculating a position of the radiation source with respect to the recording surface and/or an angle of a central axis of the radiation emitted from the radiation source with respect to the recording surface; wherein at least two lines, which pass through positions of images of the detection portions, recorded in the radiation image detector by irradiation thereof by the radiation which has passed through the detection portions, and the predetermined positions of the detection portions, are obtained; and the angle/position calculating means calculates the position of the radiation source with respect to the recording surface and/or the angle of the central axis of the radiation emitted from the radiation source with respect to the recording surface based on distances between an intersection of the at least two lines and the predetermined positions of the detection portions, or distances between the position of the intersection of the at least two lines and the positions of the images of the detection portions.

The "radiation image detector" may be of any construction as long as it records radiation images by irradiation of radiation thereon, and detects the recorded radiations image as electric signals. Examples of such radiation image detectors are: those having a stimulable phosphor sheet and detect radiation images recorded on the stimulable phosphor sheet as electric signals; solid state radiation detectors; and the like.

The "detection portions" may be of any construction as long as images thereof, based on radiation irradiated on the recording surface of the radiation image detector after having passed through the detection portions, are enabled to be distinguished from images of their surroundings. Examples of such detection portions include pinholes having a higher rate of transmittance with respect to the radiation than their surroundings, and shielded portions having a lower rate of transmittance with respect to the radiation than their surroundings. In addition, the pinholes and the shielded portions may be provided in combination.

The "positions of the detection portions" may be, for example, the center points of the detection portions, and the "positions of the images of the detection portions" may be, for example, the center points of the images of the detection portions. Any positions may be used, as long as the positions enable recognition that the positions of the detecting portions correspond to positions of the images of the detection portions.

With regard to the radiation image obtaining system of the present invention, a construction may be adopted wherein:

the images of the detection portions are recorded in the recording surface of the radiation image detector at a portion of the recording surface outside a region in which the radiation image of the subject is recorded.

The radiation image obtaining system of the present invention may further comprise:

a position adjusting means for adjusting the position of the radiation source or the radiation image detector, in the case that the position of the radiation source with respect to the recording surface, calculated by the angle/position calculating means, differs from a predetermined position of the radiation source with respect to the recording surface, so that the radiation source is positioned at the predetermined position with respect to the recording surface.

The "position of the radiation source with respect to the recording surface" refers to, for example, a relative position of the radiation source with respect to the recording surface. The "predetermined position of the radiation source with respect to the recording surface" refers to, for example, a position at a predetermined distance from the center position of the recording surface, in a perpendicular direction therefrom.

The radiation image obtaining system of the present invention may further comprise:

an angle adjusting means for adjusting the angle of the central axis of the radiation with respect to the recording surface, in the case that the angle of the central axis of the radiation with respect to the recording surface, calculated by the angle/position calculating means, is not substantially perpendicular, so that the angle of the central axis of the radiation becomes substantially perpendicular with respect to the recording surface.

The radiation image obtaining system of the present invention may further comprise:

an irradiation terminating means for terminating irradiation of radiation by the radiation source, in the case that the position of the radiation source with respect to the recording surface, calculated by the angle/position calculating means, is not within a predetermined allowable range.

The "predetermined allowable range" of "the position of the radiation source with respect to the recording surface" refers to a range of positions of the radiation source with respect to the recording surface that enables recording of appropriate radiation images.

The radiation image obtaining system of the present invention may further comprise:

an irradiation terminating means for terminating irradiation of radiation by the radiation source, in the case that the angle of the central axis of the radiation with respect to the recording surface, calculated by the angle/position calculating means, is not within a predetermined allowable range.

The "predetermined allowable range" of "the angle of the central axis of the radiation with respect to the recording surface" refers to a range of angles of the central axis of the radiation with respect to the recording surface that enables recording of appropriate radiation images.

Regarding the radiation image obtaining system of the present invention, a construction may be adopted wherein:

the amount of radiation irradiated on the angle/position detection member is less than or equal to ⅕ the amount of radiation irradiated during obtainment of the radiation image of the subject.

The radiation image detector of the present invention is a radiation image detector for recording a radiation image of a subject by irradiation thereof by radiation emitted from a radiation source, which has passed through the subject and a grid, which is provided between the radiation image detector and the radiation source, parallel to a recording surface of the radiation image detector, comprising:

an angle/position detection member provided between the radiation source and the radiation image detector, having at least two detection portions having a transmittance rate with respect to radiation emitted from the radiation source different from their surroundings, which are provided at predetermined positions with respect to the recording surface; and an angle/position calculating means for calculating a position of the radiation source with respect to the recording surface and/or an angle of a central axis of the radiation emitted from the radiation source with respect to the recording surface; wherein at least two lines, which pass through positions of images of the detection portions, recorded in the radiation image detector by irradiation thereof by the radiation which has passed through the detection portions, and the predetermined positions of the detection portions, are obtained; and the angle/position calculating means calculates the position of the radiation source with respect to the recording surface and/or the angle of the central axis of the radiation emitted from the radiation source with respect to the recording surface based on distances between an intersection of the at least two lines and the predetermined positions of the detection portions, or distances between the position of the intersection of the at least two lines and the positions of the images of the detection portions.

Regarding the radiation image detector of the present invention, a construction may be adopted wherein:

the images of the detection portions are recorded in the recording surface of the radiation image detector at a portion of the recording surface outside a region in which the radiation image of the subject is recorded.

The radiation image detector of the present invention may further comprise:

a position adjusting means for adjusting the position of the radiation source or the radiation image detector, in the case that the position of the radiation source with respect to the recording surface, calculated by the angle/position calculating means, differs from a predetermined position of the radiation source with respect to the recording surface, so that the radiation source is positioned at the predetermined position with respect to the recording surface.

The radiation image detector of the present invention may further comprise:

an angle adjusting means for adjusting the angle of the central axis of the radiation with respect to the recording surface, in the case that the angle of the central axis of the radiation with respect to the recording surface, calculated by the angle/position calculating means, is not substantially perpendicular, so that the angle of the central axis of the radiation becomes substantially perpendicular with respect to the recording surface.

The radiation image detector of the present invention may further comprise:

an irradiation terminating means for terminating irradiation of radiation by the radiation source, in the case that the position of the radiation source with respect to the recording surface, calculated by the angle/position calculating means, is not within a predetermined allowable range.

The radiation image detector of the present invention may further comprise:

an irradiation terminating means for terminating irradiation of radiation by the radiation source, in the case that the angle of the central axis of the radiation with respect to the recording surface, calculated by the angle/position calculating means, is not within a predetermined allowable range.

According to the radiation image obtaining system and the radiation image detector of the present invention, at least two lines, which pass through positions of images of the detection portions, recorded in the radiation image detector by irradiation thereof by the radiation which has passed through the detection portions, and the predetermined positions of the detection portions, are obtained; and the position of the radiation source with respect to the recording surface and/or the angle of the central axis of the radiation emitted from the radiation source with respect to the recording surface is calculated, based on distances between an intersection of the at least two lines and the predetermined positions of the detection portions, or distances between the position of the intersection of the at least two lines and the positions of the images of the detection portions. Therefore, the position of the radiation source with respect to the recording surface and/or the angle of the central axis of the radiation emitted from the radiation source with respect to the recording surface are capable of being obtained with a simple construction. Appropriate recording of radiation images is enabled by making the inclination of the central axis of the radiation with respect to the recording surface of the radiation image detector substantially perpendicular, and by making the position of the radiation source with respect to the radiation image detector appropriate, based on the obtained angle and/or position.

The radiation image obtaining system and the radiation image detector of the present invention, may adopt a construction wherein the images of the detection portions are recorded in the recording surface of the radiation image detector at a portion of the recording surface outside a region in which the radiation image of the subject is recorded. In this case, the position of the radiation source with respect to the recording surface and/or the angle of the central axis of the radiation with respect to the recording surface are enabled to be obtained, without interfering with appropriate recording of the radiation image of the subject.

The radiation image obtaining system and the radiation image detector of the present invention may further comprise:

a position adjusting means for adjusting the position of the radiation source or the radiation image detector, in the case that the position of the radiation source with respect to the recording surface, calculated by the angle/position calculating means, differs from a predetermined position of the radiation source with respect to the recording surface, so that the radiation source is positioned at the predetermined position with respect to the recording surface. In this case, the position of the radiation source with respect to the recording surface can be automatically adjusted to be appropriate.

The radiation image obtaining system and the radiation image detector of the present invention may further comprise:

an angle adjusting means for adjusting the angle of the central axis of the radiation with respect to the recording surface, in the case that the angle of the central axis of the radiation with respect to the recording surface, calculated by the angle/position calculating means, is not substantially perpendicular, so that the angle of the central axis of the radiation becomes substantially perpendicular with respect to the recording surface. In this case, the angle of the central axis of the radiation with respect to the recording surface can be automatically adjusted to be substantially perpendicular.

The radiation image obtaining system and the radiation image detector of the present invention may further comprise:

an irradiation terminating means for terminating irradiation of radiation by the radiation source, in the case that the position of the radiation source with respect to the recording surface, calculated by the angle/position calculating means, is not within a predetermined allowable range, or in the case that the angle of the central axis of the radiation with respect to the recording surface, calculated by the angle/position calculating means, is not within a predetermined allowable range. The irradiation terminating means enables avoidance of radiation image obtainment in a state in which the position of the radiation source with respect to the recording surface or the angle of the central axis of the radiation with respect to the recording surface is inappropriate. Therefore, obtainment of unnecessary radiation images is avoided. In addition, irradiation of unnecessary radiation on the subject is also avoided.

The radiation image obtaining system of the present invention may adopt a construction wherein the amount of radiation irradiated on the angle/position detection member is less than or equal to 1/5 the amount of radiation irradiated during obtainment of the radiation image of the subject. In this case, if the radiation is irradiated on the subject during recording of the images of the detection portions, for example, the radiation dose irradiated on the subject is decreased.

DESCRIPTION OF THE PREFERRED EMBODIMENTS

Hereinafter, a preferred embodiment of the present invention will be described with reference to the attached drawings.

Figure 1:
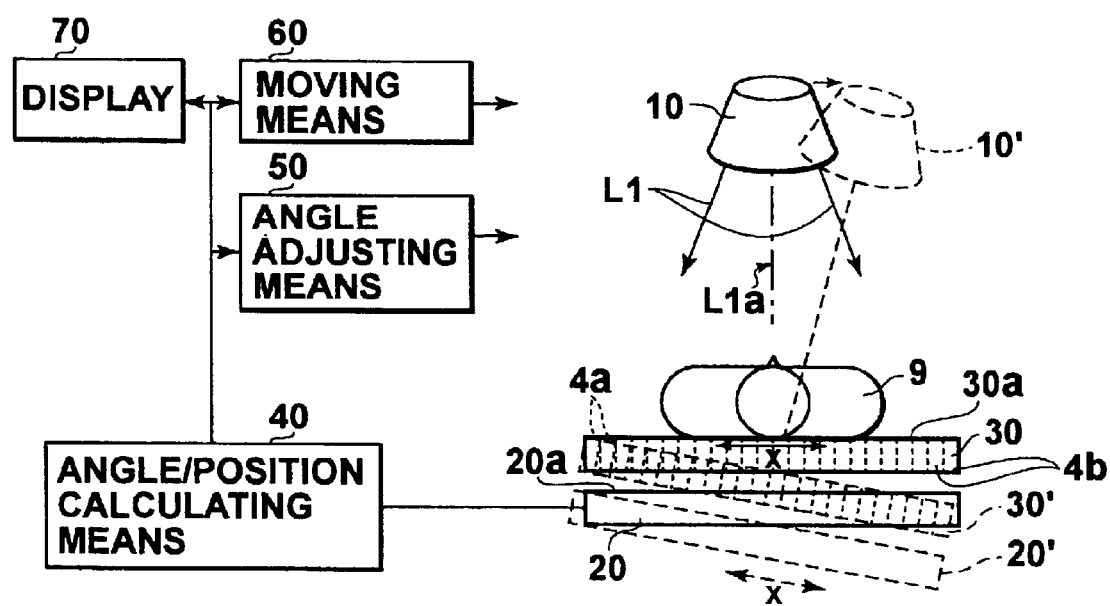
FIG. 1 is a schematic structural diagram of an embodiment of the radiation image obtaining system according to the present invention.

FIG. 1 is a schematic structural diagram of an embodiment of the radiation image obtaining system according to the present invention.

As shown in FIG. 1, the radiation image obtaining system of the present invention comprises: a radiation source 10 for emitting radiation L1; and a radiation image detector 20 for recording a radiation image by detecting radiation L2, which has been emitted from the radiation source 10 and which has passed through a subject 9. A dispersion preventing grid 30 is provided between the subject 9 and the radiation image detector 20, so that a surface 30a of the grid 30, on which the radiation L2 is incident, is parallel to a recording surface 20a of the radiation image detector 20. The radiation source 10, the radiation image detector 20, and the grid 30 are configured to be portable.

As the radiation image detector 20, one can be employed comprising: a cassette; and a stimulable phosphor sheet or a solid state radiation detector housed within the cassette. In the case that a radiation image detector comprising a stimulable phosphor sheet is employed, it is necessary to provide a readout mechanism, for irradiating a readout light on the stimulable phosphor sheet; receiving phosphorescence emitted from the sheet by irradiation of the readout light thereon; and photoelectrically converting the phosphorescence to output an image signal.

Figure 2A:
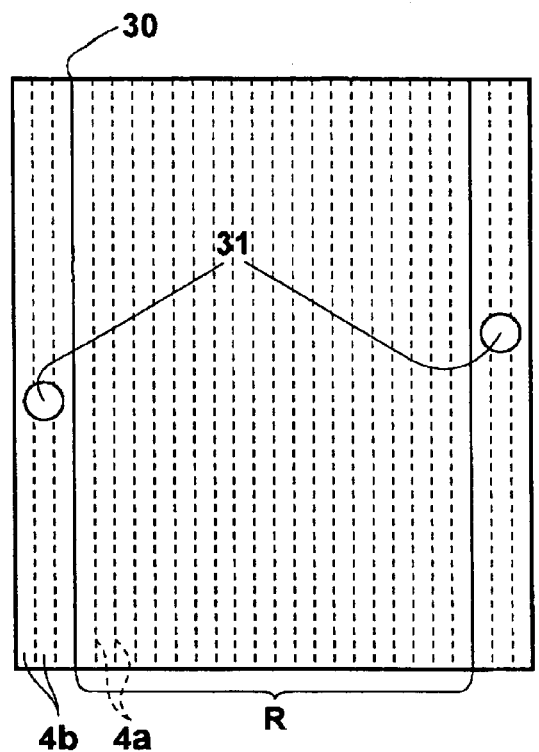
FIG. 2A is schematic plan view of a grid which is employed by the radiation image obtaining system of FIG. 1.
Figure 2B:
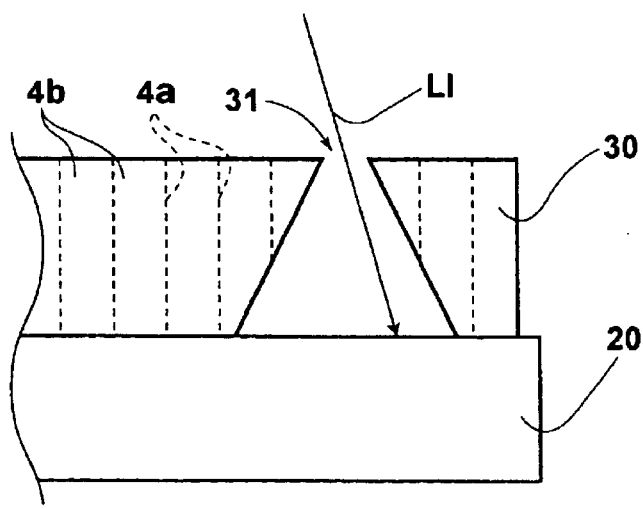
FIG. 2B is a sectional view of a portion of the grid of FIG. 2A.
Figure 3:
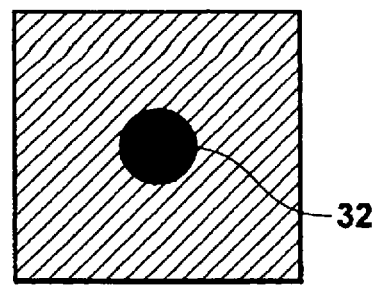
FIG. 3 shows a pinhole image detected by the radiation image obtaining system of FIG. 1.

As shown in FIG. 1, FIG. 2A and FIG. 2B, the grid 30 comprises lead 4a, which absorbs radiation, and aluminum 4b, which transmits radiation, alternately provided at a predetermined pitch. The grid 30 functions to prevent dispersion of radiation. In addition, the grid 30 of the present embodiment functions as an angle/position detection member for detecting the position of the radiation source 10 with respect to the recording surface 20a of the radiation image detector 20 and the angle of a central axis of radiation with respect to the recording surface 20a. FIG. 2A is schematic plan view of the grid 30. As shown in FIG. 2A, the grid 30 is provided with two pinholes 31 in its peripheral portion. FIG. 2B is a sectional view of a portion of the grid 30, at which the pinhole 31 is positioned, and the radiation image detector 20. As shown in FIG. 2B, the pinhole 31 is an aperture that penetrates the grid 30. The diameter of the aperture is larger on the side of the radiation image detector 20 than on the side of the radiation source 10. The radiation which passes through the pinhole 31 is directly irradiated at a predetermined position of the radiation image detector 20, and records a pinhole image 32 as shown in FIG. 3. Note that in FIG. 3, the black portion is the pinhole image 32, and the hatched portion surrounding the pinhole image 32 is an image based on radiation which passes though portions of the grid other than the pinhole 31. As shown in FIG. 3, the pinhole image 32 is recorded as an image higher in density than its surroundings. The region of the recording surface 20a in which the pinhole image 32 is recorded is outside an image region R (refer to FIG. 2A) in which a radiation image of the subject 9 is recorded. Note that in the present embodiment, the pinholes 31 are provided as detection portions. However, the detection portions are not limited to being pinholes, and may be of any construction as long as images thereof, based on radiation irradiated on the recording surface of the radiation image detector after having passed through the detection portions, are enabled to be distinguished from images of their surroundings.

The radiation image obtaining system of the present embodiment further comprises: an angle/position calculating means 40 for calculating the position of the radiation source 10 with respect to the recording surface 20a of the radiation image detector 20 and for calculating the angle of a central axis L1a of the radiation 1 with respect to the recording surface 20a of the radiation image detector 20; an angle adjusting means 50 for adjusting the angle of the central axis L1a of the radiation L1 with respect to the recording surface 20a, based on an angle signal output from the angle/position calculating means 40; a moving means 60 for moving the radiation source 10; and a display 70 for displaying whether the calculated angle and position are appropriate. The angle/position calculating means 40, the angle adjusting means 50, the moving means 60, and the display 70 are also constructed to be portable.

Regarding the construction of the moving means 60, any structure may be employed as long as it is capable of moving the radiation source 10 in an X-direction (the direction parallel to the recording surface 20a), and in a Y-direction (perpendicular to the X-direction). Regarding the construction of the angle adjusting means 50, any structure may be employed as long as it is capable of tilting the radiation image detector 20 in its X-Y plane by independent rotation in the X and the Y directions.

Next, the operation of the radiation image obtaining system according to the present embodiment will be described.

First, the radiation image detector 20 and the grid 30 are placed beneath the subject 9, and the radiation source 10 is placed above the subject 9. At this time, the grid 30 is placed on the upper side of the radiation image detector 20 so as to be parallel therewith. Then, pre-irradiation is performed by the radiation source 10 prior to actual obtainment of a radiation image of the subject 9. The pre-irradiation is performed to confirm that the position of the radiation source 10 with respect to the recording surface 20a is appropriate, and to confirm that the angle of the central axis L1a of the radiation L1 emitted from the radiation source 10 with respect to the recording surface 20a is substantially perpendicular. The amount of radiation emitted from the radiation source 10 during pre-irradiation is less than or equal to ⅕ the amount of radiation emitted during actual obtainment of a radiation image. Preferably, the amount of radiation emitted during pre-irradiation is less than or equal to 1/10 the amount of radiation emitted during actual obtainment of the radiation image.

A portion of the radiation emitted from the radiation source 10 in the above manner passes through the subject 9 and the grid 30, then is irradiated onto the recording surface 20a of the radiation image detector 20, thereby recording a radiation image of the subject 9. At this time, radiation which does not pass through the subject 9 is irradiated onto the peripheral portion of the grid 30. This radiation passes through the grid 30 and is irradiated onto the peripheral portion of the radiation image detector 20. Then, pinhole images 32 are recorded by the radiation which passes through the pinholes 31.

An image signal, based on the radiation image of the subject 9 and the pinhole images 32, is output from the radiation image detector 20, and input to the angle/position calculating means 40. The angle/position calculating means 40 determines the center positions of the two pinhole images 32, based on the image signal of the two pinhole images 32.

Then, the angle/position calculating means 40 obtains two lines that pass through the center positions of the pinhole images 32 and the pinholes 31 corresponding thereto, and an intersection of these two lines are determined. This intersection is the focal point position of the radiation source 10. Note that the center positions of the pinholes 31 are physically determined by the thickness of the grid 30 and the positions of the pinholes 31, and are set in advance in the angle/position calculating means 40.

Then, the distances between the focal point position of the radiation source 10 and the center positions of the pinhole images 32 are obtained. The angle of the central axis of the radiation with respect to the recording surface 20a is obtained based on the obtained distances. The angles based on the two distances may be prepared in a look up table or the like. The angle signal detected by the angle/position calculating means 40 is input to the angle adjusting means 50. The angle adjusting means 50 changes the inclination angle of the radiation source 10 based on the input angle signal, to make angle of the central axis L1a of the radiation L1 substantially perpendicular with respect to the recording surface 20a.

If the inclination angle of the radiation source 10 is changed, the relative position, between the central axis L1a of the radiation L1 emitted from the radiation source 10; and the radiation image detector 20 and the subject 9, shifts. Accordingly, the angle/position calculating means 40 determines the position of the radiation source 10, the angle of which has been adjusted by the angle adjusting means 50, calculates the amount of shift, and outputs the calculated amount of shift to the moving means 60. The moving means 60 moves the radiation source 10 in the X and Y directions based on the amount of shift, so that the central axis L1a of the radiation L1 is positioned substantially at the center of the recording surface 20a, or at a position in the vicinity of a portion of interest of the subject 9. A radiation source 10' in this state is indicated by the dotted lines in FIG. 1. Specifically, the operation described above is performed so as to move the radiation source 10 to the position of the radiation source 10' indicated by the dotted lines, in the case that the radiation image detector 20 is inclined with respect to the horizontal, as a radiation image detector 20' indicated by dotted lines in FIG. 1.

According to the radiation image obtaining system and the radiation image detector of the present invention, two lines, which pass through center positions of the pinhole images 32, recorded in the radiation image detector 20 by irradiation thereof by the radiation which has passed through the pinholes 31, and the predetermined center positions of the pinholes 31, are obtained; and the position of the radiation source 10 with respect to the recording surface 20a and the angle of the central axis L1a of the radiation L1 with respect to the recording surface 20a are calculated, based on distances between the intersection of the two lines the center positions of the pinhole images 32. Therefore, the aforementioned position and angle are capable of being obtained with a simple construction. Appropriate recording of radiation images is enabled by making the inclination of the central axis L1a of the radiation L1 with respect to the recording surface 20a of the radiation image detector 20 substantially perpendicular, and by making the position of the radiation source 10 with respect to the radiation image detector 20 appropriate, based on the obtained angle and position.

Note that the angle/position calculating means may determine that the angle of the radiation L1 with respect to the recording surface 20a of the radiation image detector 20 is substantially perpendicular, and only a shift in the X and Y direction exists. In this case, only the amount of shift is calculated, based on the distances between the focal point of the radiation source 10 and the center positions of the pinhole images 32. Then, movement of the radiation source 10 only is performed by the moving means 60.

In the case that the aforementioned angle or the aforementioned amount of shift, calculated by the angle/position calculating means is not within a predetermined range, a message indicating that conditions are inappropriate for obtainment of a radiation image of the subject is displayed at the display means 70. Alternatively, an alarm may be sounded in the case that conditions are inappropriate for obtainment of a radiation image of the subject.

The radiation image obtaining system and the radiation image detector of the present invention may further comprise an irradiation terminating means. The irradiation terminating means terminates irradiation of radiation by the radiation source in the case that the aforementioned angle or the aforementioned amount of shift, calculated by the angle/position calculating means is not within a predetermined range.

In the embodiment described above, the pinholes 31 were provided in the grid 30. However, the present invention is not limited to this construction. The grid 30 and an angle/position detection member, in which the pinholes 31 are provided, may be formed as separate structures. In addition, any structure may be adopted for the pinholes 31, as long as images similar to the pinhole images 32 are capable of being obtained.

Figure 4:
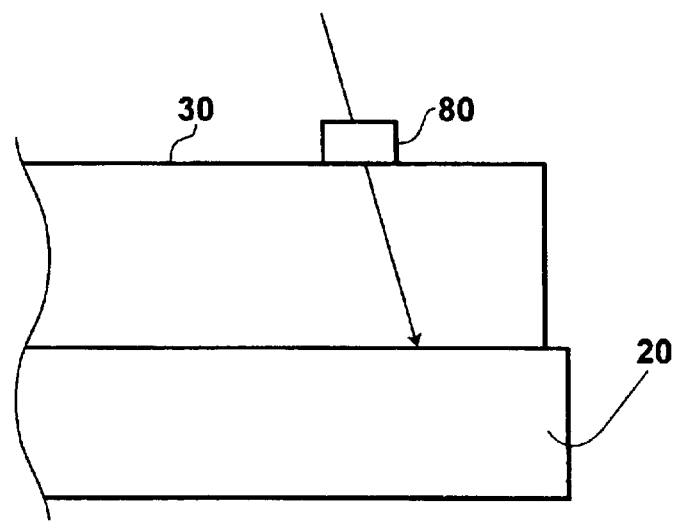
FIG. 4 shows an alternate construction of an angle/position detection member.
Figure 5:
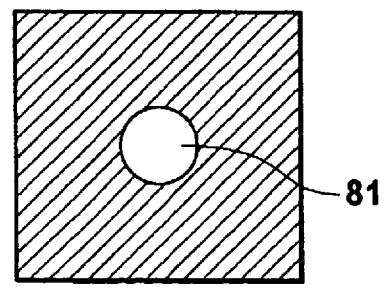
FIG. 5 shows a shielding portion image detected in the case that the angle/position detection member of FIG. 4 is employed.

In addition, in the embodiment described above, the grid 30 being provided with the pinholes 31 was employed as the angle/position detection member. However, shielding portions 80, that shield radiation, may be provided on the surface of the grid 30, as shown in FIG. 4. In this case, the shielding portion image 81 will be reverse that of the embodiment described above, as shown in FIG. 5. In the case that the shielding portions 80 are to be employed as the detection portions, the construction is not limited to the shielding portions 80 being provided on the surface of the grid 30. Any construction may be adopted, as long as images similar to the shielding portion images 81 are capable of being obtained.

In the embodiment described above, the subject 9 as well as the peripheral portion of the grid 30, at which the pinholes 31 are provided, was irradiated with radiation during pre-irradiation. However, only the peripheral portion may be irradiated during pre-irradiation. In addition, radiation may be irradiated on the subject 9 and the peripheral portion of the grid 30, at which the pinholes 31 are provided, during pre-irradiation, and irradiated only on the subject 9 during obtainment of a radiation image thereof.

In the embodiment described above, the radiation source 10 was moved based on the aforementioned angle and amount of shift calculated by the angle/position calculating means 40. However, in the case that the subject 9 is placed on a stretcher or a bed provided between the radiation source 10 and the radiation image detector 20, a construction may be adopted wherein the radiation image detector 20 and the grid 30 are moved.

What is claimed is:

1. A radiation image obtaining system comprising:

a radiation source;

a radiation image detector for recording a radiation image of a subject by irradiation thereof by radiation emitted from a radiation source, which has passed through the subject; and a grid provided between the radiation image detector and the radiation source, parallel to a recording surface of the radiation image detector;

an angle/position detection member provided between the radiation source and the radiation image detector, having at least two detection portions having a transmittance rate with respect to radiation emitted from the radiation source different from their surroundings, which are provided at predetermined positions with respect to the recording surface; and an angle/position calculating means for calculating a position of the radiation source with respect to the recording surface and/or an angle of a central axis of the radiation emitted from the radiation source with respect to the recording surface; wherein at least two lines, which pass through positions of images of the detection portions, recorded in the radiation image detector by irradiation thereof by the radiation which has passed through the detection portions, and the predetermined positions of the detection portions, are obtained; and the angle/position calculating means calculates the position of the radiation source with respect to the recording surface and/or the angle of the central axis of the radiation emitted from the radiation source with respect to the recording surface based on distances between an intersection of the at least two lines and the predetermined positions of the detection portions, or distances between the position of the intersection of the at least two lines and the positions of the images of the detection portions.

2. A radiation image obtaining system as defined in claim 1, wherein:

the images of the detection portions are recorded in the recording surface of the radiation image detector at a portion of the recording surface outside a region in which the radiation image of the subject is recorded.

3. A radiation image obtaining system as defined in claim 1, further comprising:

a position adjusting means for adjusting the position of the radiation source or the radiation image detector, in the case that the position of the radiation source with respect to the recording surface, calculated by the angle/position calculating means, differs from a predetermined position of the radiation source with respect to the recording surface, so that the radiation source is positioned at the predetermined position with respect to the recording surface.

4. A radiation image obtaining system as defined in claim 3, further comprising:

an angle adjusting means for adjusting the angle of the central axis of the radiation with respect to the recording surface, in the case that the angle of the central axis of the radiation with respect to the recording surface, calculated by the angle/position calculating means, is not substantially perpendicular, so that the angle of the central axis of the radiation becomes substantially perpendicular with respect to the recording surface.

5. A radiation image obtaining system as defined in claim 1, further comprising:

an angle adjusting means for adjusting the angle of the central axis of the radiation with respect to the recording surface, in the case that the angle of the central axis of the radiation with respect to the recording surface, calculated by the angle/position calculating means, is not substantially perpendicular, so that the angle of the central axis of the radiation becomes substantially perpendicular with respect to the recording surface.

6. A radiation image obtaining system as defined in claim 1, further comprising:

an irradiation terminating means for terminating irradiation of radiation by the radiation source, in the case that the position of the radiation source with respect to the recording surface, calculated by the angle/position calculating means, is not within a predetermined allowable range.

7. A radiation image obtaining system as defined in claim 1, further comprising:

an irradiation terminating means for terminating irradiation of radiation by the radiation source, in the case that the angle of the central axis of the radiation with respect to the recording surface, calculated by the angle/position calculating means, is not within a predetermined allowable range.

8. A radiation image obtaining system as defined in claim 1, wherein:

the amount of radiation irradiated on the angle/position detection member is less than or equal to $1/5$ the amount of radiation irradiated during obtainment of the radiation image of the subject.

9. A radiation image detector for recording a radiation image of a subject by irradiation thereof by radiation emitted from a radiation source, which has passed through the subject and a grid, which is provided between the radiation image detector and the radiation source, parallel to a recording surface of the radiation image detector, comprising:

an angle/position detection member provided between the radiation source and the radiation image detector, having at least two detection portions having a transmittance rate with respect to radiation emitted from the radiation source different from their surroundings, which are provided at predetermined positions with respect to the recording surface; and an angle/position calculating means for calculating a position of the radiation source with respect to the recording surface and/or an angle of a central axis of the radiation emitted from the radiation source with respect to the recording surface; wherein at least two lines, which pass through positions of images of the detection portions, recorded in the radiation image detector by irradiation thereof by the radiation which has passed through the detection portions, and the predetermined positions of the detection portions, are obtained; and the angle/position calculating means calculates the position of the radiation source with respect to the recording surface and/or the angle of the central axis of the radiation emitted from the radiation source with respect to the recording surface based on distances between an intersection of the at least two lines and the predetermined positions of the detection portions, or distances between the position of the intersection of the at least two lines and the positions of the images of the detection portions.

10. A radiation image detector as defined in claim 9, wherein:

the images of the detection portions are recorded in the recording surface of the radiation image detector at a portion of the recording surface outside a region in which the radiation image of the subject is recorded.

11. A radiation image detector as defined in claim 9, further comprising:

a position adjusting means for adjusting the position of the radiation source or the radiation image detector, in the case that the position of the radiation source with respect to the recording surface, calculated by the angle/position calculating means, differs from a predetermined position of the radiation source with respect to the recording surface, so that the radiation source is positioned at the predetermined position with respect to the recording surface.

12. A radiation image detector as defined in claim 11, further comprising:

an angle adjusting means for adjusting the angle of the central axis of the radiation with respect to the recording surface, in the case that the angle of the central axis of the radiation with respect to the recording surface, calculated by the angle/position calculating means, is not substantially perpendicular, so that the angle of the central axis of the radiation becomes substantially perpendicular with respect to the recording surface.

13. A radiation image detector as defined in claim 9, further comprising:

an angle adjusting means for adjusting the angle of the central axis of the radiation with respect to the recording surface, in the case that the angle of the central axis of the radiation with respect to the recording surface, calculated by the angle/position calculating means, is not substantially perpendicular, so that the angle of the central axis of the radiation becomes substantially perpendicular with respect to the recording surface.

14. A radiation image detector as defined in claim 9, further comprising:

an irradiation terminating means for terminating irradiation of radiation by the radiation source, in the case that the position of the radiation source with respect to the recording surface, calculated by the angle/position calculating means, is not within a predetermined allowable range.

15. A radiation image detector as defined in claim 9, further comprising:

an irradiation terminating means for terminating irradiation of radiation by the radiation source, in the case that the angle of the central axis of the radiation with respect to the recording surface, calculated by the angle/position calculating means, is not within a predetermined allowable range.

\* \* \* \* \*